United States Patent [19]

Nakauchi et al.

[11] Patent Number: 4,474,306

[45] Date of Patent: Oct. 2, 1984

[54] POSITIONING AND BONDING METHOD

[75] Inventors: Kenji Nakauchi; Atsushi Shiraishi, both of Kanagawa, Japan

[73] Assignee: Fuji Photo Film Co., Ltd., Kanagawa, Japan

[21] Appl. No.: 545,973

[22] Filed: Oct. 27, 1983

[30] Foreign Application Priority Data

Oct. 29, 1982 [JP] Japan .................. 57-190358

[51] Int. Cl.³ .......................................... B65D 41/00
[52] U.S. Cl. ....................................... 220/359; 156/257
[58] Field of Search ................ 220/200, 359; 156/257

[56] References Cited

U.S. PATENT DOCUMENTS 3,215,304 11/1965 Rohe ..................................... 220/359
3,825,148 7/1974 Hunter et al. ....................... 220/359
4,192,433 3/1980 Hascoe ................................ 220/359
4,331,258 5/1982 Geschwind .......................... 220/359
4,401,231 8/1983 Helms .................................. 220/359

Primary Examiner—George T. Hall
Attorney, Agent, or Firm—Sughrue, Mion, Zinn, Macpeak & Seas

[57] ABSTRACT

Two components can be positioned relative to each other and adhesively bonded together without any displacement resulting from contraction of the adhesive by forming on the first component 11 an annular protrusion 11A having its center at a point to be aligned. On the second component 12 is formed an annular groove 12A having its center at a corresponding point to be aligned. The width of the groove is significantly larger than the width of the protrusion. The protrusion is aligned within the groove and then adhesive is poured into the gaps 14 between the protrusion and the sides of the groove.

5 Claims, 5 Drawing Figures

POSITIONING AND BONDING METHOD

BACKGROUND OF THE INVENTION

This invention relates to a method for positioning and bonding components of a high precision optical system or the like.

A known photographic picture density data recording apparatus (densitometer) for a picture printing unit comprises a light source for illuminating an original negative or positive film for printing (although hereafter only a "negative" will be referred to); light receiving storage elements arranged in a planar configuration facing the negative; and an optical system for forming the image of the negative on the light receiving elements.

FIG. 1 is a side view outlining the above-described apparatus. A light source 2 illuminates a negative 1. A filter plate 3 has three color separating filters R, G, and B. The filter plate 3 is rotatable around a shaft 3A. One example of the filter plate 3 is shown in FIG. 2. A projecting lens 4 receives the light transmitted through the filter plate 4. A light receiving unit 5 comprises charge coupled devices (CCDs) arranged in a plane. The light receiving unit 5 is made up of 350 CCDs for instance for imaging 135 type film (the so-called 35 mm film). The CCDs are arranged with fourteen elements along the short side of the image and twenty-five elements along the long side.

It is essential for the above-described densitometer to accurately form the image of the negative film on the light receiving unit 5 by means of the lens 4 for a long period. However, since the light receiving unit 5 is very small (for instance 1.25 mm long and 0.7 mm wide), in forming the image of the negative on the light receiving unit 5, it is very difficult to position the lens 4 and the light receiving unit 5 for instance with a distance of about 3 mm therebetween, and to fix the parts thus positioned. Especially, where adhesive is applied to bond together the parts which have been positioned, the parts are greatly displaced by the inherent contraction of the adhesive. This presents a serious problem for the apparatus.

SUMMARY

In view of the foregoing, an object of this invention is to provide a positioning and bonding method in which precision components which have been positioned are adhesively bonded together substantially without being affected by the contraction of the adhesive.

The foregoing object of the invention has been achieved by the provision of a positioning and bonding method in which two components which have been positioned are bonded with an adhesive. According to the invention, an annular protrusion with its center at a point to be positioned is formed on one of the two components, while an annular groove with its center at the corresponding point to be positioned and with a width sufficiently larger than the wall thickness of the protrusion is formed in the other component. With the protrusion engaged within the groove, the adhesive is applied only to the portions of the gap between the protrusion and the sides of the groove where the force of contraction of the adhesive acts symmetrically with respect to the points to be positioned.

DETAILED DESCRIPTION OF THE PREFERRED EMBODIMENT

One embodiment of this invention will be described with reference to the accompanying drawings.

Figure 1:
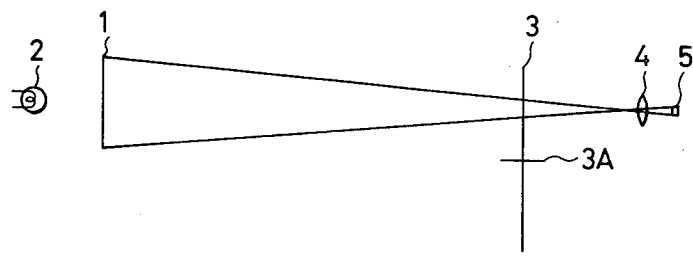
FIG. 1 is a side view of a known densitometer to which this invention is suitably applied.
Figure 2:
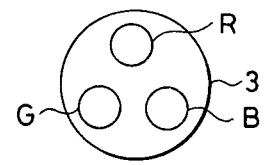
FIG. 2 is an explanatory diagram showing a color filter part of the apparatus of FIG. 1 in detail.
Figure 3:
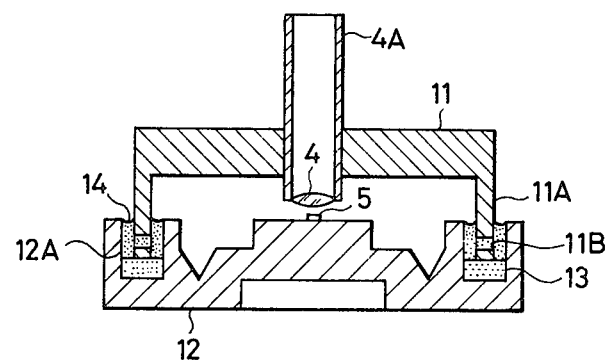
FIG. 3 is a sectional view of an assembly of components which are positioned and bonded together according to one example of a positioning and bonding method of the invention.

FIG. 3 is a vertical sectional view showing the assembly of the above-described lens 4 and light receiving unit 5 which have been positioned and bonded together according to the positioning and bonding method of the invention. The lens 4 is coupled through a lens barrel 4A to a holder 11. The holder 11 is made up of a disc-shaped base plate and an annular or ring-shaped protrusion 11A extending downward from the periphery of the base plate. The annulus 11A has a plurality of through-holes 11B which are filled with adhesive as described later.

The light receiving unit 5 is fixedly secured to a seat plate 12. An annular groove 12A is cut in the plate 12 so as to receive the annular protrusion 11A of the holder 11. The width of the groove 12A is sufficiently larger than the wall thickness of the protrusion 11A, and the gaps between the groove 12A and the protrusion 11A are filled with an adhesive to the extent that the groove and the protrusion are bonded or fixedly secured to each other, as described later. A sponge ring 13 having independent bubbles includes therein is inserted in the bottom of the groove 12A of the plate 12. The ring 13 has a suitable height (or thickness) so that the holder is positioned on it.

The above-described assembly is formed as follows: The holder 11 and the plate 12, which have been constructed as described above, are accurately positioned with a jig, to be described later, and then an adhesive is poured into the gaps between the protrusion 11A and the sides of the groove 12A so that the holder 11 and the plate 12 are fixedly secured to each other. The sponge ring 13 fitted in the bottom of the groove 12A is thick enough to contact the protrusion 11A and the protrusion 11A has the through-holes 11B for allowing adhesive to flow, as was described before. Therefore, the poured adhesive spreads in the two gaps between the groove 12A and the protrusion 11A which are formed respectively outside and inside of the protrusion 11A. After a suitable amount of adhesive has been poured, it is solidified by drying into two dried adhesive layers 14, as a result of which the holder 11 and the seat plate 12 are fixedly secured to each other.

While the adhesive is being dried, the solvent, for an example, evaporates so that the adhesive contracts. The force which is provided by the contraction, a force of contraction, acts to reduce the distances between the adhesion surfaces, i.e., to reduce the two gaps. The two dried adhesive layers 14 are formed between the confronting sides of the protrusion 11A and the groove 12A, positioned on both sides of the protrusion 11A, and disposed along the circumference of the circle whose center is the lens 4 and therefore the center of the light receiving unit 5. Accordingly, the force of contraction is substantially cancelled out on both sides of the protrusion 11A or on the circumference of the circle mentioned above; that is, it will not greatly affect the protrusion 11A and the groove 12A. As a result, the holder 11 and the seat plate 12 will not move relative to each other; that is, their positions are maintained unchanged.

Figure 4:
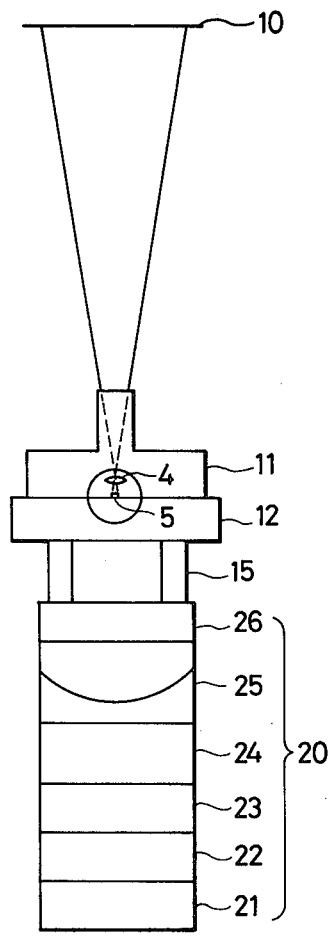
FIG. 4 is an explanatory diagram outlining a positioning operation.

FIG. 4 is a side view outlining a method of positioning the holder 11 of the lens 4 and the seat plate 12 to which the light receiving unit 5 has been secured. In FIG. 4, reference numeral 10 designates a positioning chart. A positioning jig 20 comprises an X-Y plane (horizontal plane) rotation mechanism 21, an X-direction movement mechanism 22, a Y-direction movement mechanism 23, a Z-direction (vertical direction) movement mechanism 24, a vertical plane X-direction inclination mechanism 25, and a vertical plane Y-direction inclination mechanism 26.

In positioning the holder 11 and the seat plate 12, first the holder 11 with the lens 4 is fixedly set in place with respect to the positioning chart 10. Then the seat plate 12 to which the light receiving unit 5 has been secured and which is fixedly secured through legs 15 to the top of the positioning jig 20 is combined with the already set holder 11. In the positioning operation, the image of the positioning chart 10 is formed on the light receiving unit 5 by the lens 4, and the position of the seat plate 12 is adjusted by the movement mechanisms of the positioning jig 20 according to the electrical signal output of the light receiving unit 5.

Figure 5:
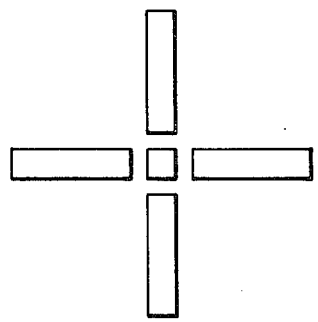
FIG. 5 is an explanatory diagram showing one example of a positioning chart.

One example of the positioning chart is as shown in FIG. 5. In adjusting the position of the seat plate 12, corrections are carried out in the following order: rotation correction by the X-Y plane rotation mechanism 21; centering by the X-direction movement mechanism 22 and the Y-direction movement mechanism 23; accurate focusing by the Z-direction movement mechanism 24; and inclination correction by the vertical plane inclination mechanisms 25 and 26. These corrections are repeated as necessary. After the positioning operation has been accomplished, the mechanisms 21-26 of the positioning jig 20 are fixed. Thereafter, the bonding adhesive is poured into the gaps 12A.

In the embodiment shown in FIG. 3, the sponge ring 13 which has independent bubbles included within is fitted in the bottom of the groove 12A of the seat plate 12 in order to prevent the entrance of the adhesive. However, it goes without saying that the ring 13 used as a spacer ring may be made of other materials. A shapeless material such as a gas stream may be emloyed instead of the solid ring.

In the embodiment, the protrusion 11A of the holder 11 for the lens 4 has a plurality of through-holes 11B for allowing the flow of adhesive, as was described above. However, it goes without saying that the number of through-holes is optional. It may be zero so that the protrusion 11A may have no through-hole. In this case, the adhesive is poured only into the gap outside the protrusion 11A, and the force of contraction is balanced by being applied to the outer wall of the protrusion 11A.

As is apparent from the above description, according to the invention, in adhesive bonding of two components which have been positioned, an annular protrusion with its center at a point which is to be positioned is provided on one of the two components, while an annular groove with its center at the corresponding point to be positioned and having a width larger than the wall thickness of the annular protrusion is formed in the other component. Under the condition that the protrusion is fitted in the groove and the two points are aligned, the adhesive is applied only to the portion of the gaps between the sides of the groove and the protrusion so that the force of the contraction of the adhesive acts symmetrically with respect to the positioned points. Accordingly, the components which have been positioned can be fixedly secured to each other without changing their positions. This effect should be highly advantageous for components to be positioned and then bonded together.

We claim:

1. A method for positioning and bonding two components, comprising the steps of:
    forming on a first component (11) an annular protrusion (11A) having its center at one point;
    forming on a second component (12) an annular groove (12A) having its center at a point that is to be positioned in alignment with said one point of the first component, said groove having a width greater than the wall thickness of said protrusion;
    positioning said first and second components with the centers of said protrusion and said groove aligned and with said protrusion positioned within said groove; and
    applying an adhesive into the gap (14) between a wall of said said and said protrusion.

2. A method for positioning and bonding, as recited in claim 1, wherein the step of forming said annular protrusion further comprises forming one or more radial through-holes (11B) in said protrusion at a position facing said gap.

3. A method for positioning and bonding, as recited in claim 1, further comprising the step of inserting a spacer ring (13) into the bottom of said ring and wherein the positioning step causes the first component to contact said spacer ring.

4. A positioned and bonded dual-component apparatus, comprising:
    a first component (11);
    a second component (12);
    an annular protrusion (11A) on the surface of said first component;
    an annular groove (12A) formed on the surface of said second component having the same radius as said annular protrusion and a width greater than the wall thickness of said annular protrusion, said annular protrusion being fit within said groove, whereby a gap (14) is formed between said protrusion and the wall of said groove; and
    adhesive filling said gap.

5. A positioned and bonded dual-component apparatus as recited in claim 4, wherein said annular protrusion has at least one radial through-hole (11B) and wherein said adhesive fills said through-hole.

* * * * *